(12) United States Patent
Lin et al.

(10) Patent No.: US 9,144,786 B2
(45) Date of Patent: Sep. 29, 2015

(54) GAS PHASE HETEROGENEOUS CATALYTIC OXIDATION OF ALKANES TO ALIPHATIC KETONES AND/OR OTHER OXYGENATES

(71) Applicant: EVERNU TECHNOLOGY LLC, Warminster, PA (US)

(72) Inventors: Manhua Lin, Warminster, PA (US); Xiang Wang, Nanchang (CN); Younghoon Yeom, Woodbridge, NJ (US)

(73) Assignee: Ever Nu Technology, LLC, Warminster, PA (US)

( * ) Notice: Subject to any disclaimer, the term of this patent is extended or adjusted under 35 U.S.C. 154(b) by 0 days.

(21) Appl. No.: 14/602,552

(22) Filed: Jan. 22, 2015

(65) Prior Publication Data

US 2015/0141239 A1  May 21, 2015

Related U.S. Application Data

(63) Continuation of application No. 14/116,424, filed as application No. PCT/US2012/037033 on May 9, 2012, now Pat. No. 8,981,157.

(60) Provisional application No. 61/485,837, filed on May 13, 2011.

(51) Int. Cl.

| | | |
|---|---|---|
| *B01J 23/00* | (2006.01) | |
| *B01J 21/00* | (2006.01) | |
| *B01J 35/00* | (2006.01) | |
| *B01J 37/00* | (2006.01) | |
| *B01J 23/28* | (2006.01) | |
| *C07C 45/33* | (2006.01) | |
| *B01J 21/08* | (2006.01) | |
| *B01J 23/30* | (2006.01) | |
| *B01J 35/10* | (2006.01) | |
| *B01J 37/02* | (2006.01) | |
| *C07C 29/50* | (2006.01) | |
| *C07C 45/34* | (2006.01) | |
| *B01J 37/04* | (2006.01) | |
| *B01J 37/08* | (2006.01) | |
| *B01J 38/02* | (2006.01) | |
| *B01J 38/12* | (2006.01) | |
| *B01J 23/92* | (2006.01) | |

(52) U.S. Cl.
CPC *B01J 23/28* (2013.01); *B01J 21/08* (2013.01); *B01J 23/002* (2013.01); *B01J 23/30* (2013.01); *B01J 35/1004* (2013.01); *B01J 35/1014* (2013.01); *B01J 35/1023* (2013.01); *B01J 37/0036* (2013.01); *B01J 37/0201* (2013.01); *B01J 37/04* (2013.01); *B01J 37/08* (2013.01); *C07C 29/50* (2013.01); *C07C 45/33* (2013.01); *C07C 45/34* (2013.01); *B01J 23/92* (2013.01); *B01J 38/02* (2013.01); *B01J 38/12* (2013.01); *B01J 2523/00* (2013.01); *C07C 2101/14* (2013.01)

(58) Field of Classification Search
CPC ........... B01J 23/00; B01J 21/00; B01J 35/00; B01J 35/37; C07C 45/33
USPC ................................. 502/243, 305, 307, 323
See application file for complete search history.

(56) References Cited

U.S. PATENT DOCUMENTS

| | | | | |
|---|---|---|---|---|
| 5,380,933 | A * | 1/1995 | Ushikubo et al. | 562/549 |
| 6,156,920 | A * | 12/2000 | Brazdil et al. | 558/319 |
| 6,514,902 | B1 * | 2/2003 | Inoue et al. | 502/305 |
| 6,514,903 | B2 * | 2/2003 | Lin et al. | 502/311 |
| 2008/0177106 | A1 * | 7/2008 | Lin et al. | 562/549 |

FOREIGN PATENT DOCUMENTS

WO     WO2010/014206 A1 *  2/2010

OTHER PUBLICATIONS

Hettige et al. Cyclohexane oxidation and carbon deposition over metal oxide catalysts. Chemosphere 43 (2001), 1079-1083.*

* cited by examiner

*Primary Examiner* — Sikarl Witherspoon

(57) ABSTRACT

A catalyst, its method of preparation and its use for producing aliphatic ketones by subjecting alkanes $C_3$ to $C_9$ to a gas phase catalytic oxidation in the presence of air or oxygen, and, optionally, steam and/or one or more diluting gases. The catalyst comprises a catalytically active mixed metal oxide phase and a suitable support material onto and/or into which the active catalytic phase is dispersed.

12 Claims, No Drawings

GAS PHASE HETEROGENEOUS CATALYTIC OXIDATION OF ALKANES TO ALIPHATIC KETONES AND/OR OTHER OXYGENATES

CROSS-REFERENCE TO RELATED APPLICATIONS

The present application is a continuation of U.S. patent application Ser. No. 14/116,424, filed Jan. 9, 2014, which is the U.S. National Stage of International Application No. PCT/US2012/037033, filed May 9, 2012, which claims the benefit of U.S. Provisional Patent Application No. 61/485,837, filed May 13, 2011. The entire disclosure of each of the aforesaid application is incorporated by reference in the present application.

STATEMENT REGARDING FEDERAL SPONSORED RESEARCH OR DEVELOPMENT

The present invention was made with funds provided by the United State Department of Energy under Grant Nos. DE-F002-03ER83652 and DE-FG02-05ER84321. The U.S. Government has certain rights in this invention.

FIELD OF THE INVENTION

The present invention relates to a composition and methods of preparation of a supported mixed metal oxide catalyst, and the use of the catalyst for the production of aliphatic ketones and/or other oxygenates. For example, ketones having a carbon number from 3 to 9 and/or one or more other oxygenates are produced from the gas phase heterogeneous catalytic oxidation of an alkane of the same number of carbon, wherein oxygen, air or other oxygen-containing gas is used as oxidant. The alkane can be of acyclic, cyclic, or a substituted cyclic structures, such as n-butane, cyclohexane or methylcyclohexane. The corresponding $C_3$-$C_9$ aliphatic ketones can be saturated or unsaturated or a mixture thereof, such as methyl ethyl ketone (MEK) and/or methyl vinyl ketone (MVK), from the oxidation of n-butane, or cyclohexanone from the oxidation of cyclohexane. Other valuable products (oxygenates) of such oxidations include the corresponding alcohol and/or aldehyde derived from the alkane, such as cyclohexanol from the oxidation of cyclohexane or butyraldehyde from the oxidation of n-butane.

The present invention concerning catalytic alkane oxidation is particularly exemplified by the preparation and the use of several supported mixed metal oxide catalysts in chemical processes wherein air was used as the oxidant and wherein MEK and MVK were produced from the gas phase heterogeneous catalytic oxidation of n-butane, and cyclohexanone and cyclohexanol were produced from the gas phase heterogeneous catalytic oxidation of cyclohexane.

BACKGROUND OF THE INVENTION

Saturated or unsaturated aliphatic ketones or alcohols, such as methyl ethyl ketone (MEK), methyl vinyl ketone (MVK), cyclohexanone and cyclohexanol, are important chemicals used in various applications in the chemical and pharmaceutical industries. They are important intermediates and are among the most preferred organic solvents or reagents used in producing other more valuable specialty chemicals or pharmaceutical products. For example, MEK is a stable and low viscosity aliphatic ketone partially miscible in water while completely miscible with most organic solvents. This exceptional solvency makes MEK the second most important (next to acetone) commercially produced ketone for use as an organic solvent in various industrial applications, including coating and paints, adhesives, tapes, and lube oil de-waxing, etc. As another example, MVK is an effective alkylating agent and a useful intermediate with applications in organic synthesis, including the syntheses of pharmaceutical products such as vitamins or steroids. By way of further example, cyclohexanone, in addition to serving as a common organic solvent and reagent, is used as the precursor for making caprolactam, the monomer used for the production of Nylon-6. By way of yet another example, cyclohexanol is the alcohol component of KA oil, a mixture of ketone cyclohexanone and alcohol cyclohexanol. KA oil is the key intermediate for the production of both Nylon-6 and Nylon-6,6.

With respect to the conventional manufacturing of MEK, the most widely used commercial process is a three-step sec-butyl alcohol process, commonly known as the SBA process, which starts with the oxidation of 1-butene in sulfuric acid followed by hydrolysis, acid stripping, neutralization and separation leading to sec-butyl alcohol, which subsequently undergoes gas phase catalytic dehydrogenation with oxides of Cu, Zn or Cr as the catalysts to produce MEK [*Ullmann's Encyclopedia of Industrial Chemistry*, (2001) $6^{th}$ Ed.]. There are many drawbacks of the SBA process, mainly relating to the higher manufacturing cost associated with the use of 1-butene as the starting material; the usage and recycling of a large quantity of corrosive sulfuric acid; the multiple steps of oxidation, hydrolysis, neutralization and separation as well as the treatment of a large quantity of acid sludge and other toxic waste generated in the process. Beside the economic drawbacks, the environmental pollution that results from the large quantity of toxic waste generated is very serious, while the energy consumption required for all the production and cleanup steps is substantial. Another commonly used commercial process for the production of MEK is the liquid phase oxidation of n-butane. In this liquid phase process, acetic acid is used as solvent, cobalt and sodium acetates are the homogeneous catalysts, under which condition, n-butane is oxidized by air in the liquid phase to MEK. Although this liquid phase process has been practiced for more than half a century, it is not efficient for MEK production because most of the MEK thus formed is further oxidized to acetic acid and other by-products, due to the difficulty in preventing such further oxidation in the process.

With respect to the conventional manufacturing process for cyclohexanone, cyclohexanol, or the corresponding ketone-alcohol mixture KA oil, the two most used processes are the liquid phase cyclohexane oxidation and phenol hydrogenation. The classical liquid-phase cyclohexane process, developed in the 1940s, is still a preferred process for the industrial production of KA-oil today [*Industrial Organic Chemistry*, Wiley-VCH Press, (2003) $4^{th}$ Ed]. In the liquid phase at about 150° C. under high pressure, cyclohexane is oxidized to KA-oil with cobalt salts as the catalysts. Typically, the classical process achieves around 4% cyclohexane conversion and 3.4% yield of KA oil. To improve the extremely low efficiency of this classical liquid-phase process, a modified process involving boric acid was developed in the 1950s. The boric-acid modified process increased the one-pass conversion of cyclohexane somewhat to around 10% and the KA yield to about 9%. This improved conversion rate, however, is achieved at the expense of serious pollution and increased operation costs, as "large amount of solids [wastes] need to be separated and decomposed and boric acid has to be recycled". The conventional liquid-phase cyclohexane process has since been characterized as "the least efficient of all major industrial chemical processes" [U. Schuchardt et al, *Synlett* 10

(1993) 713]. At the present time, the main drawbacks for liquid phase cyclohexane oxidation are still the low efficiency, pollution and high energy consumption.

The economic incentive to overcome such low efficiency is huge, and has continuously driven research and development efforts worldwide. The majority of such R&D efforts are concerned with modifications of the catalyst system with respect to a wide spectrum of factors ranging from metal element, oxidation state, morphology, chelating agents for organometallic complexes, host or support materials, to catalyst preparation method, etc. Similarly, exploring alternative non-air oxidants, such as hydrogen peroxide and tert-butyl hydroperoxide, has continued to be a topic of interest for many researchers. However, none of the modifications of the liquid-phase process have thus far achieved any higher efficiency than the boric-acid modification, and all of these modifications usually come with a set of new problems. Indeed, it seems that the conclusion by the recent review [U. Schuchardt et. al, *Appl. CataL A. Gen,* 211 (2001) 1] is still fairly accurate that "cyclohexane oxidation [in liquid phase] continues to be a challenge".

In contrast to the extensive research and development efforts devoted to improving the liquid-phase catalytic process for the production of corresponding ketones from alkanes, very few publications have appeared concerning the catalytic production of aliphatic ketones by gas phase oxidation of alkanes. While gas-phase catalytic oxidation of n-butane over VPO catalysts has been well studied and was successfully commercialized in the 1980s, it is for the production of maleic anhydride, and not for the production of any ketones [N. Ballarini, et al, *Topics in Catalysis,* 38 (2006) 147]. Insofar as is known, no publication to date has described the production of a measurable amount of MEK from n-butane catalytic reaction in the gas phase. Likewise, very few publications have appeared concerning the production of cyclohexanone by gas-phase catalytic oxidation of cyclohexane.

U.S. Pat. No. 2,386,372 to Wagner is directed to solid catalysts of metal or metal oxides of Ag, Cr, Cu, Fe, V etc. for the oxidation of cyclohexane to cyclohexanone. The actual example described therein is the oxidation of methylcyclohexane. However, extensive follow-up research on cyclohexane gas-phase catalytic oxidation over 11 solid catalysts, including most of the catalysts claimed in U.S. Pat. No. 2,386,372, revealed that $CO_2$ and water were the only products found [W. Hoot and K. Kobe, *J. Ind. & Eng. Chem.,* 47 (1955) 776]. It was only in recent years that any further attempts at gas phase catalytic oxidation of cyclohexane were reported, such as those over Zn—Cr—O catalyst [F. Patcas et al, *Progress in Catalysis,* 8 (1999) 54], over several other oxide catalysts containing transition metals V, Mn, Ni, Cu, Zn and Mo etc. [C. Hettige, et al, *Chemosphere,* 43 (2001) 1079], and over $CuO_x$ oxides supported on $SiO_2$ and fiberglass [J. Medina-Valtierra et al, Appl. Cat. A, 238 (2003) 1]. Except for the cyclohexane oxidation over the supported $CuO_x$ catalysts (wherein cyclohexanone and cyclohexanol were reported among many other products), all of the other above-mentioned attempts confirmed the early conclusion by Hoot and Kobe that a) $CO_2$ was the main product, and b) no cyclohexanone or cyclohexanol were detected in the product streams. The present inventors attempted to reproduce the oxidation of cyclohexane over the $CuO_x$ catalyst supported on $SiO_2$. However, benzene and $CO_2$ were the only products detected, while no cyclohexanone could be found when cyclohexane was subjected to gas phase oxidation over the $CuOx/SiO_2$ catalyst (comparative example-5). The present inventors also investigated a silica supported Au catalyst (comparative example-6) which is said to catalyze the selective oxidation of cyclohexane to cyclohexanone in the liquid phase [K. Zhu et al, *Catal. Letter.* 100 (2005) 195]. This supported gold catalyst, $Au/SiO_2$, was found to be slightly different from the $CuOx/SiO_2$ catalyst in that $CO_2$ was the only product detected from the cyclohexane gas phase oxidation.

Hence, there is a longstanding need for an innovative process involving a novel catalyst useful for the production of aliphatic ketones from heterogeneous catalytic oxidation of C3-C9 alkanes in the gas phase.

SUMMARY OF THE INVENTION

The present invention relates to a composition and methods of preparation of a supported catalyst comprising a catalytically active mixed metal oxide phase dispersed onto and/or into a suitable support, and the use of the catalyst in a chemical process wherein oxygen, air or other oxygen-containing gas is used as the oxidant and wherein an aliphatic ketone having a carbon number from 3 to 9 and/or one or more other valuable oxygenates are produced from the gas phase heterogeneous catalytic oxidation of an alkane of the same carbon number.

According to one aspect, the present invention provides a solid catalyst composition comprising a catalytically active mixed metal oxide phase and a suitable support material onto and/or into which the active catalytic phase is dispersed. The active catalytic phase of metal oxide comprises a compound having the formula $A_aB_bX_xO_n$, wherein A is at least one of the group of elements Mo, Nb, Ta, Ti, W and Zr; B is at least one of the group of elements Cs, K, Li, Na, and Rb; and X, if present, is at least one of the group of elements Al, Ba, Ca, Dy, Fe, Ga, La, Mg, Pd, Pr, Si, Sr, V and Zn, in addition to the elements of groups A and B; and wherein a=1, b is 0.01 to 20, x is 0 to 1, and n is dependent on the oxidation state of the other elements. A suitable support material comprises high surface area and thermally stable carbide, nitride, graphite or oxide material, the oxide being selected from the groups of $Al_2O_3$, $Ce_2O_3$, $CeO_2$, $La_2O_3$, MgO, $Nb_2O_5$, $SiO_2$, $TiO_2$, $Y_2O_3$, $Yb_2O_3$ and $ZrO_2$, or a composite thereof, the multi-dimensional shape or form of which has no restriction. There is also no particular restriction as to the relative weight percentage of the catalytically active metal oxide phase or that of support material in the final catalyst.

In a second aspect, the present invention provides methods or processes for preparing the aforementioned supported catalyst comprising a catalytically active metal oxide phase and a suitable multi-dimensional support material onto and/or into which the active catalytic phase is dispersed, or otherwise incorporated. Typically, a catalyst precursor is a substance containing all of the essential elements of the active metal oxide phase and either the preformed support material or the essential element of the support material. The catalyst precursor is prepared and subsequently subjected to heat treatment or calcination under conditions that yield a thermally stable supported catalyst. In preparing the catalyst precursor, the elements of the active phase and either a pre-formed support material or the essential elements of the support material can be brought together, combined, and/or admixed by using any suitable techniques or methods known in the art. A thermally stable supported mixed metal oxide catalyst may also be obtained without the final calcination step, by dispersing, using techniques or methods known in the art, appropriately sized particles of a pre-formed active metal oxide phase onto or into a pre-formed support material of multi-dimensional structure.

A third aspect of the present invention further provides a chemical process wherein the aforementioned supported catalyst is used in the presence of a air or oxygen-containing atmosphere to produce aliphatic ketones containing 3 to 9 carbons ($C_3$-$C_9$), with or without one or more other valuable oxygenates from the heterogeneous catalytic oxidation of an alkane of the same carbon number in the gas phase.

DETAILED DESCRIPTION OF THE INVENTION

In the first aspect, the present invention provides a supported solid catalyst comprising a catalytically active mixed metal oxide phase and a suitable support material, onto and/or into which the active catalytic phase is incorporated. The active catalytic metal oxide phase comprises a compound having the formula $A_a B_b X_x O_n$, wherein A is at least one of the group of elements Mo, Nb, Ta, Ti, W and Zr; B is at least one of the group of elements Cs, K, Li, Na and Rb; and X, if present, is at least one of the group of elements Al, Ba, Ca, Dy, Fe, Ga, La, Mg, Pd, Pr, Si, Sr, V and Zn, in addition to the elements of groups A and B; and wherein a=1, b is 0.01 to 20, x is 0 to 1, and n is dependent on the oxidation state of the other elements. A suitable support material is at least one of the group of high surface area and thermally stable materials such as carbide, nitride, graphite or oxide material, including but not limited to, $Al_2O_3$, $Ce_2O_3$, $CeO_2$, $La_2O_3$, MgO, $Nb_2O_5$, $SiO_2$, $TiO_2$, $Y_2O_3$, $Yb_2O_3$ and $ZrO_2$, or a composite thereof, the shape or form of which has no restriction. There is also no particular restriction as to the relative weight percentage of the catalytically active metal oxide phase or that of support material in the final catalyst.

Preferably, in the catalytically active phase A is at least one of the group of element Mo, Nb, Ta or W; B is at least one of the group of elements Cs, K and Rb; and X, if present, is at least one of the group of elements Ba, Ca, Dy, La, Li, Mg, Na, Pd, Pr, Sr and Zn; and the support comprises at least one high surface area oxide selected from the group of $La_2O_3$, MgO, $Nb_2O_5$, $SiO_2$, $TiO_2$, $Y_2O_3$, $Yb_2O_3$ and $ZrO_2$, or a composite thereof.

In a particularly preferred embodiment of the supported catalyst composition of this invention, A is Mo; B is at least one of the group of elements Cs and Rb; and X, if present, is at least one of the group of elements Ba, Ca, Dy, La, Li, Na, Pr and Zn, a=1, b is 0.1 to 10, x is 0 to 0.5, and the support material is at least one high surface area oxide selected from the group of MgO, $Nb_2O_5$, $SiO_2$, $TiO_2$ and $ZrO_2$, or a composite thereof.

The source chemical for elements of the aforementioned active phase or the support materials can be selected from, but not limited to, metals, oxides, halides, nitrates, alkoxides, oxalates, hydroxides, acetates or various organometallic compounds. The form of these source chemicals can be, among others, a liquid, a solution, a slurry or a solid.

Although there are no specific restrictions, the aforementioned support material can be of a porous or a non-porous structure with a wide range of surface structures and areas and can assume diverse multi-dimensional shapes and forms, including, but not limited to, particles, fibers, felts, ceramic foam and/or monolith. The support material can further be coated on or incorporated into certain three dimensional matrices or structures made of appropriate thermally conductive materials. While there are no specific restrictions, the preferred weight percentage of the catalytically active phase in the resulting supported mixed metal oxide catalyst is from about 0.5% to about 50.

In the second aspect, the present invention provides methods or processes for preparing the aforementioned supported catalyst comprising a catalytically active metal oxide phase and a suitable multi-dimensional support material onto and/or into which the active catalytic phase is dispersed or otherwise incorporated.

In one embodiment of the present invention, the aforementioned supported catalyst is obtained by subjecting a catalyst precursor to calcination under appropriate conditions. The catalyst precursor is a solid substance containing all of the essential elements of the active metal oxide phase and either a pre-formed multi-dimensional support material or the essential elements of the support material.

The catalyst precursor can be prepared by dispersing the elements of the active phase, together or sequentially, onto and/or into a pre-formed multi-dimensional support material, by using any techniques or methods known in the art. Such techniques or methods include, but are not limited to wetness and incipient wetness impregnation, ion-exchange, coating, chemical or metal vapor deposition and other thin layer or atomic layer deposition techniques.

The catalyst precursor can also be prepared by combining, admixing, or bringing together the appropriate source chemicals or intermediates of the active phase and the appropriate source chemicals or intermediate of the support material before, during or after the formation of the structure of the active phase or that of the support material, using any techniques or methods known in the art. Such techniques and methods include, but are not limited to sol-gel, co-gel, hydrothermal synthesis, co-precipitation, wet-mixing of solutions or slurries, and combination or dry-mixing of solid source materials or intermediates or composites thereof.

When source materials for elements of the active metal oxide phase and those for the support are combined in solid forms, the resulting solid mixture or composite can be further ground to enhance the thorough mixing of source materials/intermediates for all the elements. When the source material(s) for one or more elements is (are) introduced as a solution or a slurry, the liquid substances used in making the solution or slurry can be selected from water or various organic liquids/solvents, such as alcohols, ketones, ethers, acids, and aliphatic or aromatic compounds. Subsequently, the liquid substance(s) and/or solvent(s) can be removed using various methods known in the art, including, but not limited to, air-drying, freeze-drying, spray drying, filtration, rotary evaporation, or evaporation under a normal or reduced pressure and under normal or various elevated temperatures.

In the aforementioned embodiments of the present invention, the catalyst precursor thus formed is subjected to calcination under appropriate conditions to form a thermally stable supported oxide catalyst. The calcination may be carried out in air or under an inert atmosphere, such as under nitrogen, argon, helium or mixtures thereof. Calcination of the catalyst precursor under an inert atmosphere is preferred. The calcination is performed at an elevated temperature from about 150° C. to about 800° C., preferably from 400° C. to 600° C. The calcination may advantageously be carried out in separate stages within the stated ranges. Typically, the calcination is performed for duration of time from about 1 to about 24 hours, preferably from about 2 to about 10 hours, to obtain a stable and supported mixed metal oxide catalyst.

In still another embodiment of the present invention, a thermally stable supported mixed metal oxide catalyst may also be obtained without the final calcination step by dispersing, using techniques or methods known in the art, pre-formed and appropriately sized particles of the active metal oxide phase onto or into a pre-formed support material of multi-dimensional structure. Such techniques or methods include, but are not limited to, wet or dry-grinding of the active metal oxides phase and support material and coating or dispersing the fine particles onto or into the pre-formed multidimensional support material.

The thermally stable supported mixed metal oxide catalyst thus obtained according to the present invention can be used directly, or ground and molded to form pellets of desirable shape and size suitable for application(s) in a catalytic oxidation of alkanes.

In the third aspect, the present invention further provides a chemical process wherein the supported mixed metal oxide catalyst prepared according to the present invention is used in the presence of air or an oxygen-containing atmosphere to produce aliphatic ketones containing 3 to 9 carbons ($C_3$-$C_9$) with or without one or more other valuable oxygenates from the gas phase heterogeneous catalytic oxidation of an alkane of the same number of carbons.

In a particular embodiment of the present invention concerning a heterogeneous catalytic oxidation in the gas phase, a typical feed gas is a mixture of an alkane, air and/or oxygen, a diluting gas and desirable amounts of water vapor or steam. The diluting gas can be an inert gas such as nitrogen, argon or helium, or a gas such as carbon dioxide or the like. The presence of water vapor or steam may function as a diluting gas. The presence of water vapor may also have the benefit of suppressing over-oxidation of the desirable oxygenated products. More specifically, the feed-gas according to the present invention is a mixture of A) gas or vapor of a $C_3$ to $C_9$ alkane; B) oxygen and/or air, C) inert diluting gas(es), such as nitrogen or argon or helium or carbon dioxide, and D) steam. The molar ratio of alkane/(oxygen or air)/inert dilute gas/steam A:B:C:D of the feed-gas mixture can be, but is not limited to, (1):(0.1 to 20):(0 to 20):(0 to 70). Great care always should be taken to ascertain that the hydrocarbon to oxygen ratio in the feed-gas mixture entering the reactor, as well as in the gaseous mixture in the reaction zone and the reactor outlet, is maintained outside of the flammable region for such a mixture.

While the detailed mechanism of the catalytic oxidation of alkanes described herein is not yet fully understood, it is believed that the oxidation is sustained by the molecular oxygen present in the feed gas (either from air or oxygen). However, oxidation of a $C_3$-$C_9$ alkane in the gas phase is also possible in the absence of oxygen-containing feed gas. In such a case, the lattice oxygen atoms in the metal oxide catalyst are consumed during the oxidation of the hydrocarbons while the active phase of the catalyst is reduced accordingly. As such, an enhanced selectivity to the desired ketones or other oxygenate(s), if produced, may be obtained in the absence of molecular oxygen in the feed gas. In that case, however, a separate step for the regeneration of the mixed metal oxide catalyst would be required. For instance, the reduced metal oxide catalyst can be regenerated by exposure to an atmosphere containing molecular oxygen or other oxygen-containing sources under suitable conditions.

The heterogeneous catalytic oxidation of alkane in the gas phase can take place in a fixed bed reactor or a fluidized bed reactor. This reaction can be conducted at atmospheric pressure or under a slightly elevated pressure. A suitable reaction temperature for such an oxidation is from about 250° C. to about 600° C., but preferably is from about 300° C. to about 525° C. The heterogeneous catalytic oxidation can take place on the surface of the supported catalyst when feed-gas flows passing through the hot bed of catalyst. The space velocity (SV) of the feed-gas flow can be, but is not limited to the range of about 360 to about 36,000 to $hr^{-1}$, which corresponds to contact time of feed-gas and catalyst in a range of about 10 to about 0.1 seconds.

In another particular embodiment of the present invention, $C_3$-$C_9$ aliphatic ketones and other partial oxidation products of the same number of carbons are the desired products, when the corresponding $C_3$-$C_9$ alkane is subjected to the catalytic oxidation in the gas phase using the supported mixed metal oxide catalyst described herein. However, other oxidation or dehydrogenation products with fewer carbon atoms and lesser value may also be produced in such a reaction as by-products. In addition, unreacted alkane is also inevitably mixed with the oxidative products in the outlet stream, which need be and can easily be separated and subsequently recycled to the feed gas using conventional technologies and other methods known in the art, since the boiling point(s) of the unreacted alkane(s) are far lower than that product oxygenates.

EXAMPLES

The present invention will now be described more specifically by using Examples and Comparative Examples, wherein the conversion (Conv) and selectivity (Sel) have the following definition:

Conversion (%)=(moles of hydrocarbon consumed/moles of hydrocarbon feed)×100;

Selectivity (%)=(moles of product formed/moles of hydrocarbon consumed)×100;

These examples are provided for illustrative purposes only, and are in no way intended to limit the scope of the present invention, as set forth in the claims. The general procedures used for the preparation of catalyst precursor are provided as follows.

Impregnation Methods and Processes

Impregnation is a method well known in the art used for the preparation of a supported catalyst or its precursor. By impregnation, the element(s) of an active catalyst is dispersed onto or into the support material through either wet or dry processes.

In a wet-impregnation, typically, the source chemical for element M, if a liquid, is used directly or diluted with a solvent, and if a solid, is dissolved in a suitable solvent (water, organic solvents, or a mixture of) to form a solution. The solution, in a desirable amount, is combined with a pre-formed solid support material, such as alumina ($Al_2O_3$) or silica ($SiO_2$) to form a wet mixture, from which the solvent is subsequently removed to obtain a solid material with element M sufficiently dispersed to the support material. The removal of solvent(s) can be accomplished by evaporation under an elevated temperature, achieved by using temperature controlling devises such as a hotplate, an oven or a rotavap. Impregnation of multiple elements can also be accomplished in the same manner by making a solution containing all of the elements, or by sequential impregnations of one or more elements at a time. Wet impregnation techniques used in the examples include incipient wetness where the amount of solvent is limited to the pore volume of the support material, and other techniques where excess amount of solvent is used.

In dry-impregnation, the element(s) of an active catalyst is dispersed to the support material without the use of any solvent or liquid. Examples of dry-impregnation include, but not limited to chemical vapor deposition or metal vapor deposition.

Example 1

Catalyst-1 with composition according to Table-1 (3% $Mo_1K_1O_n$ supported on $SiO_2$) was prepared as follows. Ammonium heptamolybdate tetrahydrate (($N_4$)$_6$ $Mo7O_{24} \cdot 4H_2O$) and potassium nitrate ($KNO_3$) were used as the source for Mo and K respectively, and silica ($SiO_2$) was used as the support material. The catalyst precursor was prepared by using wet-impregnation method followed by the removal of the solvent in an oven at 80° C. for 8 hours. Water was the solvent used in making solutions of source materials for the wet-impregnation. The catalyst precursor was subsequently calcined at 550° C. in air for 4 hours to obtain a final catalyst. Following the specific reaction condition described in Table 1, about 0.5 g of the catalyst was packed in a quartz tubular reactor of 4 mm ID and subjected to n-butane oxidation under atmospheric pressure. Gas-flow-controllers were used to control the flow rates of all gases. The amount of water vapor was controlled by the temperature of the water saturator and the amount of air/nitrogen passing through. The reaction effluent was sampled hot without condensation and was analyzed using a HP5890 GC equipped with both FID and TCD detectors to determine the alkane conversion and the selectivity of all of the oxidation products. The results of n-butane catalytic oxidation are shown in Table 1.

Example 2 and 3

Catalyst-2 (11% $Mo_1Cs_1Zn_{0.01}O_n/SiO_2$) and Catalyst-3 (12% $Mo_1Cs1Na0.04Pr_{0.01}O_n/SiO_2$) with composition according to Table-1 were prepared in the same manner as described in Example-1, except the solvent removal was performed by the use of a rotavap. In addition, cesium nitrate, zinc chloride, sodium chloride and praseodymium nitrate ($CsNO_3$, $ZnCl_2$, $NaCl$ and $Pr(NO_3)_3$) were used as the source chemicals for Cs, Zn, Na, and Pr respectively. The alkane catalytic reaction was also conducted in the same manner as described in Example-1. The specific reaction conditions and results of n-butane oxidation are also shown in Table 1.

Example 4 and 5

Catalyst-4 (8% $Mo_1Rb_1O_n/SiO_2$) and Catalyst-5 (8% $Mo_1Cs_1O_n/SiO_2$) with composition according to Table-2 were prepared in the same manner as described in Example-2. In addition, rubidium nitrate ($RbNO_3$) was used as the source chemical for Rb. The alkane catalytic oxidation was conducted in the same manner as described in Example-1, except cyclohexane was the alkane for the oxidation, and the amount of cyclohexane in the feed-gas mixture was controlled by the amount of air/nitrogen bubbling through a cyclohexane vapor saturator and the temperature of the saturator. The specific reaction conditions and results of cyclohexane oxidation are shown in Table 2. Cyclohexanone and cyclohexanol in the reaction effluent were analyzed and reported as a mixture. However, cyclohexanone is the major component of the mixture.

Example 6

Catalyst-6 (20% $Mo_1Cs_1O_n/SiO_2$) with composition according to Table-2 was prepared in the same manner as described in Example-1, except cesium hydroxide (50% CsOH solution) was used as the source of Cs and the catalyst precursor was calcined at 450° C. under argon. The catalyst thus obtained was tested in the same manner as described in Example-4 and the specific reaction condition and results are shown in Table 2.

Example 7

Catalyst-7 (8% $WCs_4O_6/SiO_2$) was prepared according to composition shown in Table-2. Solid metal oxide having empirical formula $WCs_4O_6$ was first prepared from cesium carbonate ($Cs_2CO_3$) and ammonium metatungstate (($NH_4$)$_6$ $H_2W_{12}O_{40}$) by the mixing and evaporation of the corresponding solutions. The catalyst was obtained subsequently by mixing and grinding of the solid metal oxide and the $SiO_2$ support material. The catalytic oxidation took place in the same manner as described in Example-4. The specific reaction condition and results of cyclohexane oxidation are shown in Table 2.

TABLE 1

Examples of MEK/MVK Formation in n-Butane Oxidation

| | Catalyst Composition Active Phase/ Support | Feed molar ratio nC4/air/$N_2$/$H_2O$ Space Velocity (SV) | Temp. (° C.) | nC4 Conv. (%) | Selectivity (%) | | | | |
|---|---|---|---|---|---|---|---|---|---|
| | | | | | MEK | MVK | BA | BE | $CO_2$ |
| E-1 | 3% $Mo_1K_1O_n/SiO_2$ | 1/5/15/21, SV = 5160 | 475 | 18 | 15 | 4 | 1 | 7 | 48 |
| E-2 | 11% $Mo_1Cs_1Zn_{0.01}O_n/SiO2$ | 1/19/20/41, SV = 2460 | 450 | 29 | 23 | 9 | 3 | 7 | 40 |
| E-3 | 12% $Mo_1Cs_1Na_{0.04}Pr_{0.01}O_n/SiO_2$ | 1/11/29/42, SV = 4302 | 475 | 29 | 23 | 15 | 4 | 9 | 23 | nC4 is n-butane,

MEK is methyl ethyl ketone,

MVK is methyl vinyl ketone;

BA is butyraldehyde,

BE is butenes

TABLE 2

Examples of Cyclohexanone/Cyclohexanol Formation in Cyclohexane Oxidation

| | Catalyst composition | Feed gas volume ratio * CHA/air/N2/H20 | Temp | CHA conv. | Selectivity (%) | | |
|---|---|---|---|---|---|---|---|
| | Active Phase/ Support | Space Velocity (SV) | (°C.) | (%) | CHO & CHOH | Ben | $CO_2$ |
| E-4 | 8% $Mo_1Rb_1O_n/SiO_2$ | 1/4/3/7, SV = 4800 | 400 | 14 | 23 | 2 | 65 |
| E-5 | 8% $Mo_1Cs_1O_n/SiO2$ | 1/4/3/7, SV = 4800 | 400 | 12 | 45 | 2 | 47 |
| E-6 | 20% $Mo_1Cs_1O_n/SiO_2$ | 1/5/7/12, SV = 5160 | 370 | 11 | 62 | 1 | 24 |
| E-7 | 8% $WCs_4O_6/SiO_2$ | 1/5/7/12, SV = 5160 | 470 | 6 | 28 | 11 | 40 |

CHA is cyclohexane,
CHO&CHOH is mixture of cyclohexanone & cyclohexanol,
BEN is benzene
* In describing feed gas volume ratio CHA/air/N2/H2O, CHA is the volume of air-flow from a CHA saturator maintained at 26° C., and H2O is the volume of air and N2 flow from a H2O saturator at 26° C.

TABLE 3

Comparative examples of prior-art catalysts in n-butane oxidation

| | Catalyst Composition | Prior-art for Catalyst preparation | Feed molar ratio nC4/air/$N_2$/$H_2O$ Space Velocity (SV) | Temp (°C.) | nC4 Conv. (%) | Selectivity (%) | | | | |
|---|---|---|---|---|---|---|---|---|---|---|
| | | | | | | MEK | MVK | BE | AcOH | $CO_2$ |
| CE-1 | $Mo_1V_{0.3}O_n$ | U.S. Pat. No. 5,380,933 U.S. Pat. No. 6,514,903 | 1/11/29/42 SV = 2150 | 440 | 2 | 2 | 3 | 17 | 0 | 71 |
| CE-2 | $Mo_1V_{0.3}Te_{0.2}Nb_{0.1}O_n$ | U.S. Pat. No. 5,380,933 U.S. Pat. No. 6,514,903 | 2/26/0/42, SV = 2640 | 350 | 30 | 0.3 | 0 | 0 | 5 | 88 | nC4 is n-butane,
MEK is methyl ethyl ketone,
MVK is methyl vinyl ketone;
BE is butenes,
AcOH is acetic acid,

TABLE 4

Comparative examples of prior-art catalysts in cyclohexane oxidation

| | Catalyst Composition | Prior-art for Catalyst preparation | Feed gas volume ratio * CHA/air/$N_2$/$H_2O$ Space Velocity (SV) | Temp (°C.) | CHA conv. (%) | Selectivity (%) | | |
|---|---|---|---|---|---|---|---|---|
| | | | | | | CHO & CHOH | Ben | $CO_2$ |
| CE-3 | $Mo_1V_{0.3}Te_{0.2}Nb_{0.1}O_n$ | U.S. Pat. No. 5,380,933 U.S. Pat. No. 6,514,903 | 1/5/7/12 SV = 2580 | 400 | 23 | 0 | 76 | 22 |
| CE-4 | $Mo_1Sb_{0.5}Ce_{0.09}Sn_{0.005}Ag_{0.001}O_n$ | U.S. Pat. No. 7,888,281 | 1/47/0/51 SV = 2632 | 500 | 20 | 0 | 71 | 27 |
| CE-5 | 3.2% $CuO/SiO_2$ | J. Medina-Valtierra et al, Appl. Cat. 238 (2003) 1 | 1/3/4/7 SV = 4800 | 300 | 36 | 0 | 30 | 70 |
| CE-6 | 1% $Au/SiO_2$ | K. Zhu et al, Catal. Letter.100 (2005) 195 | 1/3/4/7 SV = 4800 | 430 | 4.4 | 0 | 0 | 100 |

CHA is cyclohexane,
CHO&CHOH is mixture of cyclohexanone & cyclohexanol,
BEN is benzene
* In describing feed gas volume ratio CHA/air/N2/H2O, CHA is the volume of air-flow from a CHA saturator maintained at 26° C., and H2O is the volume of air and N2 flow from a H2O saturator at 26° C.

Comparative Example 1 and 2

Comparative catalyst-1 and -2 with composition according to Table-3 were prepared according to procedures disclosed in U.S. Pat. Nos. 5,380,933 and 6,514,903. The alkane catalytic reaction was conducted in the same manner as described in Example-1, hereinabove. The to specific reaction conditions and results of n-butane oxidation are shown in Table-3.

Comparative Example 3 and 4

Comparative catalyst-3 and -4 with composition according to Table-4 were prepared according to procedures disclosed in U.S. Pat. Nos. 5,380,933, 6,514,903 and 7,888,281 respectively. The alkane catalytic reaction was conducted in the same manner as described in Example-4 hereinabove. The specific reaction conditions and results of cyclohexane oxidation are shown in Table 4.

Comparative Example 5 and 6

Comparative catalyst-5 and -6 with composition according to Table-4 were prepared according to procedures disclosed by J. Medina-Valtierra et al (*Appl. Cat.* A, 238 (2003) 1) and by K. Zhu et al (*Catal. Letter.* 100 (2005) 195) respectively. Cupric acetate Cu(OAc)$_2$ and HAuCl$_4$ were used as the source of Cu and Au respectively. The Au/SiO$_2$ catalyst in CE-6 was obtained after the subsequent H$_2$ treatment of the precursor. The alkane catalytic reaction was conducted in the same manner as described in Example-4, hereinabove. The specific reaction conditions and results of cyclohexane oxidation are shown in Table 4.

The entire disclosure of every patent and non-patent publication cited in the foregoing specification is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. The supported, mixed metal oxide catalyst, its methods of preparation and use can in alternate embodiments, be more specifically defined by any of the transitional terms "comprising", "consisting essentially of" and "consisting of".

References Cited

| Patents Document | | |
|---|---|---|
| U.S. Pat. No. 2,386,372 | October 1945 | Wagner |
| U.S. Pat. No. 5,380,933 | January 1995 | Ushikubo et al |
| U.S. Pat. No. 6,514,903B | February 2003 | Lin et al |
| U.S. Pat. No. 7,888,281 | February 2011 | Lin et al |

Other Publications
1 W. Neier, G. Strehlke, *Ullmann's Encyclopedia of Industrial Chemistry*, "2-Butanone", 6$^{th}$ Ed., Electronic Release (2001)
2 K. Weissermel, H. Arpe, *Industrial Organic Chemistry*, Wiley-VCH Press, 2$^{nd}$ Edition 1993, 3$^{rd}$ Edition 1997, and 4$^{th}$ Edition 2003
3 U. Schuchardt, W. Carvalha, E. Spinace, *Synlett* 10 (1993) 713;
4 U. Schuchardt, D. Cardoso et. al, *Applied Catalysis, A. Gen*, 211 (2001) 1
5 VPO catalyst for n-butane oxidation to maleic anhydride: A goal achieved, or a still open challenge? By Ballarini, N.; Cavani, F. et al, *Topics in Catalysis* 38(1-3), (2006), 147-156.
6 Vapor-phase air oxidation of cyclohexane, W. Hoot and K. Kobe, *J. of Ind. & Eng. Chem.*, (1955), 47, 776-781
7 a. Cyclohexane oxidation over Zn—Cr—O catalysts, By F. Patcas et al, *Progress in Catalysis* (1999), 8(2), 54.
  b. Cyclohexane oxidation and carbon deposition over metal oxide catalysts, By C. Hettige, et al, *Chemosphere* (2001), 43(8), 1079
8 Cyclohexane oxidation over Cu2O—CuO and CuO thin films deposited by CVD process on fiberglass, By Medina-Valtierra, Jorge; Ramirez-Ortiz, Jorge; et al *Applied Catalysis, A: General* (2003), 238(1), 1
9 a. K. Zhu et al, *Cabal Letter.* 100 (2005) 195;
  b. Zhao et al, *Chem. Commun.*, 2004, 904-905.

What is claimed is:

1. A supported catalyst comprising a catalytically active mixed metal oxide phase and a suitable multi-dimensional support material onto and/or into which the catalytically active phase is incorporated and wherein the catalytically active phase comprises a compound having the formula A$_a$B$_b$X$_x$O$_n$ wherein A is at least one of the group of elements Mo, Nb, Ta, Ti, W, and Zr; B is at least one of the group of elements Cs, K, Li, Na and Rb; and X, if present, is at least one of the group of elements Al, Ba, Ca, Dy, Fe, Ga, La, Mg, Pd, Pr, Si, Sr, V and Zn in addition to the elements of groups A and B; and wherein a=1, b is 0.01 to 20, x is 0 to 1, and n is dependent on the oxidation state of the other elements, and the support comprises at least one high surface area and thermally stable carbide, nitride, graphite or oxide material, said oxide being selected from the group of Al$_2$O$_3$, Ce$_2$O$_3$, CeO$_2$, La$_2$O$_3$, MgO, Nb$_2$O$_5$, SiO$_2$, TiO$_2$, Y$_2$O$_3$, Yb$_2$O$_3$ and ZrO$_2$, or a composite thereof.

2. The catalyst according to claim 1, wherein catalytically active phase A is at least one of the group of element Mo, Nb, Ta and W; B is at least one of the group of elements Cs, K and Rb; and X, if present, is at least one of the group of elements Ba, Ca, Dy, La, Li, Mg, Na, Pd, Pr, Sr and Zn, and wherein the support material is at least one high surface area oxide, selected from the group of La$_2$O$_3$, MgO, Nb$_2$O$_5$, SiO$_2$, TiO$_2$, Y$_2$O$_3$, Yb$_2$O$_3$ and ZrO$_2$, or a composite thereof.

3. The catalyst according to claim 1, wherein catalytically active phase A is Mo; B is at least one of the group of elements Cs and Rb; and X, if present, is at least one of the group of elements Ba, Ca, Dy, La, Li, Na, Pr and Zn, a=1, b is 0.1 to 10, x is 0 to 0.5, and the support material is at least one high surface area oxide selected from the group of MgO, Nb$_2$O$_5$, SiO$_2$, TiO$_2$ and ZrO$_2$, or a composite thereof.

4. The catalyst according to claim 1, wherein the support material has a high surface-area of tens to hundreds of square meters per gram (m$^2$/g), a porous or non-porous primary structure and porous and multi-dimensional secondary structure, and a form selected from the group of particles, fibers, felts, foam or monolith, and wherein the weight percentage of the catalytically active phase in the resulting supported mixed metal oxide catalyst is from about 0.5% to about 50%.

5. The catalyst according to claim 1, wherein the support material comprises one or more of oxides of La$_2$O$_3$, MgO, Nb$_2$O$_5$, SiO$_2$, TiO$_2$, Y$_2$O$_3$, Yb$_2$O$_3$ and ZrO$_2$ or a composite thereof.

6. The catalyst according to claim 1, wherein said catalytically active mixed metal oxide phase is incorporated with said support materials as a thin layer or monolayer on the external and/or internal surfaces of the support material.

7. A process for preparing the supported, catalytically active mixed metal oxide catalyst of claim 1, the process comprising:
  a) preparing a solid catalyst precursor containing all elements of said catalytically active phase and all elements of said support material by combining the source materials of the elements wherein the source materials are selected from the group of source chemicals, intermediates, or pre-formed active phase or support material of said formulas, and wherein optionally one or more liquids are used and subsequently removed in the process of preparing said solid catalyst precursor; and b) subjecting the solid catalyst precursor to heat treatment or calcination at a temperature from about 150° C. to about 800° C. for a duration of about 1 to about 24 hours under an atmosphere containing air or one or more inert gas selected from the group of argon, nitrogen and helium, and thereby producing the supported catalyst.

8. A process for preparing a supported catalyst according to claim 7, wherein said solid catalyst precursor is prepared (i) in the presence of one or more liquids by incorporating the appropriate source chemicals of the elements of the active phase, together or sequentially, onto and/or into-a pre-formed support material using one or more methods selected from the group of wet impregnation, incipient wetness, ion-exchange, coating, wet-mixing of solution, slurry or solid, or chemical or metal vapor deposition, or (ii) in the absence of one or more liquids by dry-mixing or grinding of solid source materials or intermediates or composites thereof.

9. A process for preparing a supported catalyst according to claim 7, wherein the solid catalyst precursor is prepared in the presence of one or more liquids by combining the appropriate source material of the elements of the active phase and the source materials of the support material using one or more methods selected from the group of sol-gel, co-gel, hydrothermal synthesis, co-precipitation, wet-mixing of solution, slurry or solid, or dry-mixing or grinding of solid source materials or intermediates or composites thereof.

10. The process according to claim 7, wherein said liquid substance(s) is (are) selected from water and/or one or a mixture of organic liquids, selected from the group of alcohols, ketones, ethers, acids, aliphatic or aromatic compounds, and wherein said liquid(s) is (are) subsequently removed to yield the solid catalyst precursor using one or more techniques or methods selected from the group of air-drying, rotary evaporation, freeze-drying, spray drying, filtration, or evaporation under a normal or reduced pressure, and evaporation at normal or elevated temperatures.

11. The process according to claim 7, wherein the catalyst precursor is subjected to heat treatment or calcination at a single stage or multiple stages with an optional low-temperature stage at temperature from about 150° C. to about 350° C., and at least one high-temperature stage at temperature from about 400° C. to about 600° C.

12. The process according to claim 7, wherein the catalyst precursor is subjected to heat treatment or calcination under an inert atmosphere of argon or nitrogen or a mixture thereof.

* * * * *